(12) United States Patent
Giuseppin et al.

(10) Patent No.: US 11,753,451 B2
(45) Date of Patent: Sep. 12, 2023

(54) POTATO PROTEIN ISOLATES (71) Applicant: Coöperatie AVEBE U.A., Veendam (NL)

(72) Inventors: Marco Luigi Federico Giuseppin, Gieten (NL); Marc Christiaan Laus, Haren (NL); Jan Schipper, Emmen (NL)

(73) Assignee: Coöperatie AVEBE U.A., Veendam (NL)

( * ) Notice: Subject to any disclaimer, the term of this patent is extended or adjusted under 35 U.S.C. 154(b) by 1015 days.

(21) Appl. No.: 16/261,733

(22) Filed: Jan. 30, 2019

(65) Prior Publication Data
US 2019/0248842 A1 Aug. 15, 2019

Related U.S. Application Data (63) Continuation of application No. 14/413,058, filed as application No. PCT/NL2013/005022 on Jul. 10, 2013, now abandoned.

(30) Foreign Application Priority Data

Jul. 11, 2012 (EP) .................................... 12175944

(51) Int. Cl.
| | | |
|---|---|---|
| C07K 1/14 | (2006.01) |
| C07K 14/415 | (2006.01) |
| A23J 1/00 | (2006.01) |
| A23J 3/14 | (2006.01) |
| C07K 1/16 | (2006.01) |

(52) U.S. Cl.
CPC ............. *C07K 14/415* (2013.01); *A23J 1/006* (2013.01); *A23J 3/14* (2013.01); *C07K 1/165* (2013.01)

(58) Field of Classification Search
CPC .................................................. C07K 14/415
See application file for complete search history.

(56) References Cited

U.S. PATENT DOCUMENTS

2007/0092960 A1 4/2007 Hansen et al.

FOREIGN PATENT DOCUMENTS

| | | |
|---|---|---|
| CN | 101631599 A | 1/2010 |
| EP | 1920662 A1 | 5/2008 |
| JP | 6157599 | 3/1994 |
| WO | 9808603 A1 | 3/1998 |
| WO | 2004082397 A1 | 9/2004 |
| WO | WO2008056977 A1 | 5/2008 |

(Continued)

OTHER PUBLICATIONS

Andersson et al., "Isolation of Potato Proteins Using Simulated Moving Bed Technology," Biotechnology and Bioengineering, Dec. 15, 2008, vol. 101, No. 6, pp. 1256-1662.

(Continued)

*Primary Examiner* — Elizabeth Gwartney
(74) *Attorney, Agent, or Firm* — HOFFMANN & BARON, LLP (57) ABSTRACT

The present invention relates to a process for obtaining a potato protein fraction using a specific absorbent. Specifically, the invention relates to the carrier material, which comprises a specific polymeric material, functionalised with suitable ligands. By the use of a functionalised support carrier according to the present invention, a potato protein fraction can be obtained with higher effectiveness.

17 Claims, 1 Drawing Sheet

(56) References Cited

FOREIGN PATENT DOCUMENTS

| WO | 2008069651 A1 | | 6/2008 |
|---|---|---|---|
| WO | WO 2008/069650 | * | 6/2008 |
| WO | WO2008069650 A1 | | 6/2008 |
| WO | 2008/086811 A1 | | 7/2008 |
| WO | WO2008092450 A1 | | 8/2008 |

OTHER PUBLICATIONS

Racusen et al., "A Major Soluble Glycoprotein of Potato Tubers," Journal of Food Biochemistry, 1980, vol. 4, pp. 43-52.
Narayanan et al. "Determination of agarose gel pore size: Absorbance measurements vis a vis other techniques," Journal of Physics: Conference Series 28, 2006, pp. 83-86.
Strætkvem et al., "Expanded bed adsorption for recovery of patatin from crude potato juice", Bioseparation 7: 333-345, 1999.

* cited by examiner

POTATO PROTEIN ISOLATES

This is a continuation of U.S. patent application Ser. No. 14/413,058, filed Jan. 6, 2015, which is a U.S. National Phase of International Application No. PCT/NL2013/050522, filed Jul. 10, 2013, which claims priority to EP 12175944.3 filed Jul. 11, 2012, all of which are incorporated herein by reference in their entirety.

FIELD

The invention is in the field of food proteins, in particular isolation of a potato protein fraction.

BACKGROUND

Fresh potato juice is a complex mixture of soluble and insoluble material. It has a high protein content, and further comprises residual starch, minerals, toxic glycoalkaloides, and monomeric and polymeric reactive phenols. It is a by-product of potato starch production, and generally seen as waste.

Potato juice contains a relatively high amount of proteins, up to 1.5% by weight. They can be divided into three groups: (i) a high molecular weight (HMW) fraction of highly homologous acidic 43 kDa glycoproteins (40-50 w % of total potato protein), (ii) basic low molecular weight (LMW) 5-25 kDa among which are glycoproteins (30-40 w % of total potato protein) and (iii) other proteins (10-20 w % of total potato protein). Patatin is a family of glycoproteins that has lipid acyl hydrolase and transferase activities and will predominantly be part of the HMW fraction. The LMW fraction typically comprises protease inhibitors and other proteins generally with a low molecular weight.

Despite potato juice being considered waste, the nutritional quality of potato proteins is greater than that of casein and comparable to that of whole egg. Potato protein is rich in lysine and theoretically an excellent supplement for lysine-poor proteins such as those of cereals. Despite its unique nutritional qualities, potato protein is currently only used as animal feed, because the available products exhibit a number of serious drawbacks.

One of the major drawbacks is that it is difficult to isolate potato proteins in native form. The recovery of potato protein from the effluent of potato starch mills is commonly carried out on an industrial scale by heat coagulation, which leads to denatured potato protein. In denatured form, the proteins are devoid of their desirable functional properties, such as emulsifying capacity, foaming capacity, thermogelling capacity, water binding capacity, and the like. Even the most essential requirement for its application in the food industry, i.e. solubility in water, cannot be met.

Prior attempts to isolate the proteins from the potato juice by more mild methods, such as membrane filtration and precipitation techniques have proven to be inefficient in the industrial scale production environment. This is because of heavy membrane fouling and concomitant loss of flux and separation ability. Also, such methods lack separation ability between the various protein classes present in potato juice. Membrane filtration, for example, cannot separate the high molecular weight protein product from polymerised phenolic compounds or polysaccharides since the membrane will tend to retain them all.

Native potato proteins have been isolated before industrially. WO 2008/069650 in the name of Coöperatie Avebe U.A. discloses a process for the isolation of native potato protein isolates with low glycoalkaloid content. The process comprises flocculation and subsequent expanded bed absorption to absorb the potato proteins to an absorbent, and subsequently eluting the native potato protein isolate. This process however is expensive, and the mixed mode ligands used in the Expanded Bed absorption are relatively unstable in potato juice.

WO 2008/092450 in the name of Upfront Chromatography discloses a method for the large-scale fractionation and isolation of potato proteins using ligands and pH-based fractionation. However, the ligands are found to be sensitive to oxidative processes in potato juice, and though the addition of sulfite mitigates this problem, it does not prevent it completely. Relatively fast oxidative degradation of the ligands remains a problem. Furthermore, there is no notice of the influence of porosity on the absorption capacity, so that absorption capacities vary heavily with different absorbents. For this reason, many of the ligands mentioned in this publication are not suitable at all for the purpose of isolating potato proteins by stable operation on a cost effective industrial scale.

Thus, there remains a need for an improved method of isolating a native potato protein fraction. This invention pertains to the finding that the nature of the ligand used in absorption material, the means of coupling the ligand to this absorption material and the porosity of the absorbent material each has a strong influence on the efficiency of the absorption of potato proteins. Thus, an optimised method for the isolation of a native potato protein fraction is presented.

SUMMARY OF THE INVENTION

This invention relates to a method for the isolation of a native potato protein fraction. Specifically, a method for the fractionation of potato proteins by isoelectric point is discussed, allowing for the isolation of two fractions, being a high molecular weight fraction, and a low molecular weight fraction. The fractions can be obtained without fouling, and further purification to remove coloured compounds is not required.

DETAILED DESCRIPTION

The invention relates to a process for the isolation of a native potato protein fraction from potato juice, comprising a) adjusting the pH of the potato juice to 4.0-6.5; b) contacting the potato juice with a functionalised support carrier having pores wherein at least 90% of pores have a pore diameter between 10 and 200 nm, and wherein the carrier is functionalised with a hydrophobic, mixed-mode ligand having a pKa 2.5-5, preferably 4-5, which ligand is coupled to the carrier through an S- or O-atom, preferably a thioether group; c) desorbing the potato protein fraction from the functionalised support carrier by elution and d) optionally concentrating and/or drying the potato protein fraction.

For the present invention, potato juice is understood to mean any kind of potato-derived liquid that contains a significant amount of native potato proteins, and includes among others potato fruit juice (PFJ) that is normally obtained as a by-product of starch production, as well as diluted PFJ known as potato fruit water (PFW). Thus, it can be used in the form in which it is generally considered a waste stream, for instance from the production of potato starch, or from the processing of consumption potatoes, both in diluted or in partially processed form.

Potato juice can also be depleted of a particular fraction of potato proteins, such as for example obtained after application of a process according to the present invention. For example, potato juice that has been cleared or partially cleared of the protease inhibitor fraction, referred to as the low molecular weight (LMW)-fraction, is called LMW-depleted or partially LMW-depleted potato juice. Also, potato juice that has been cleared or partially cleared of the patatin fraction, referred to as the high molecular weight (HMW)-fraction, is called HMW-depleted or partially HMW-depleted potato juice. Also these are considered potato juice for use in a process according to the present invention.

Functional groups, as defined herein, are groups that incur significant chemical reactivity to a molecule, that results in alteration of the molecule or group under consideration. This chemical reactivity is principally defined by reactivity in a reducing water-environment, such as found in potato juice. As such, highly stable groups such as aromatic rings not substituted with a group activating the aromatic ring sufficiently to significantly alter the group in such environment (unactivated aromatic rings) are not considered functional groups for the scope of the invention. Thus phenyl rings and heterocycles such as unactivated pyridine-derivatives are not considered functional groups for the scope of the invention.

A coupling group, as used herein, is an atom or group of atoms through which the ligand is coupled to the carrier. It has formed by the chemical reaction coupling the ligand to either the spacer or the support carrier, or coupling the spacer to the support carrier.

The backbone, as used herein, is the chain of atoms which connects the ligand with the support carrier, including the coupling group(s). More in particular, it is the shortest chain of atoms which linearly connects the ligand with the support carrier.

The high molecular weight (HMW) or patatin rich fraction of potato proteins has most commercial interest, because this fraction is more difficult to obtain in pure and native form than the low molecular weight (LMW)-fraction, which is rich in protease inhibitors. Also, it is the most homogeneous fraction of potato proteins. For this reason, the present invention focuses on the isolation in native form of proteins in the HMW fraction, which comprises predominantly the heat and acid labile patatin. This is achieved through concomitant isolation of the LMW-fraction of potato proteins. As both products in pure and native form are economically interesting as long as the isolation efficiency is high, the present discovery is understood to also pertain to the isolated LMW-fraction of potato protein.

Crude potato juice is potato juice that has not undergone any purification and can be used as such, or first be subjected to a non-invasive pre-treatment that does not affect the content and nature of the potato proteins included in the juice. Such treatments may for instance be pH-adjustment, clarification or colour removal, such as done by centrifugation, filtration, flocculation and/or absorption. Specifically, various processes exist for pre-cleaning potato juice, with the aim of removing for instance unwanted contaminants, such as for instance glycoalkaloids, (poly)phenols, pectins, lipids, fatty acids and/or proanthocyanidines and coloured derivatives thereof, such as epicatechins and anthocyanines. Processes for removing one or more of these contaminants, specifically glycoalkaloids, are described in pending applications WO 2008/056977, describing absorption of contaminants from a potato juice process stream by contact with a layered silicate. Alternatively, WO 2008/069651 describes absorption of contaminants from an aqueous solution of a vegetable process stream by contact with activated carbon. A process comprising pre-treatment of the potato juice before application of the process of the present invention may be especially advantageous when using a pre-treatment comprising a flocculation process, for example with bivalent metal ions such as calcium or magnesium salts.

The isoelectric point (IEP) of a protein is the pH-value at which as much positive charge is present on the amino acids as there is negative charge. For this reason, at the IEP, a protein has a net neutral charge. When subjecting a protein to a pH below its IEP, the protein has a net positive charge, and when subjecting a protein to a pH above its IEP a protein has a net negative charge. The IEP can be determined by standard procedures such as isoelectric focussing (IEF).

In a preferred embodiment using the functionalised support carrier described herein the proteins can be fractionated to isoelectric point, and concomitantly by molecular weight. This allows separating a potato protein fraction, such as for instance a patatin fraction or a protease inhibitor fraction. A special aspect of the present invention is that one or more potato protein fractions can be bound onto the functionalised support carrier, and fractionated to obtain one or more native potato protein fractions. The potato proteins bind to the ligands on the functionalised support carrier presented herein without excessive concomitant binding of coloured potato juice components, and the functionalised support carrier is stable to deterioration and/or degradation by components of potato juice.

The process of the invention can be performed in two different modes, referred to as selective absorption and selective elution. Because of the two different modes of use of the present invention, the invention can be used for obtaining all potato proteins present in potato juice as a mixture comprising the LMW- and the HMW-fraction. Also, the invention can be used to fractionate potato proteins from potato juice into a HMW- and/or a LMW-fraction. Elution is preferably carried with an aqueous buffer.

In one mode of the invention, a potato protein fraction is obtained by selective absorption. In this mode, the pH of the potato juice is adjusted in step a) of the invention to between 4.0 and 6.5, preferably 6.0. Subsequently in step b) of the invention the potato juice is contacted with a functionalised support carrier in which at least 90% of pores have a pore diameter between 10 and 200 nm, and wherein the carrier is functionalised with a hydrophobic, mixed-mode ligand having a pKa 2.5-5, preferably 4-5, which ligand is coupled to the carrier through an S- or O atom, preferably a thioether group. Step b) of this mode results in the selective absorption of the LMW-fraction of potato protein, and as a consequence, the potato juice after contact with the functionalised support carrier is depleted of the LMW-fraction of potato protein. This results in LMW-depleted potato juice. In step c) of this embodiment, the LMW-fraction of potato protein is desorbed from the functionalised support carrier by acidic elution at a pH lower than 3 (acidic elution) or at pH higher than 9 (alkaline elution). Acidic elution eventually results in a protein product with a better quality with respect to colour, odour and taste.

In another mode of the invention, both HMW potato proteins and LMW potato proteins, if present, are first absorbed to the functionalised support carrier as a protein mixture comprising the HMW- and the LMW-fraction, if present, of potato protein. Therefore, the method pertains to absorption of the total potato protein fraction. In this mode, potato juice can be crude or pre-treated potato juice as described above, in which case both the HMW and the LMW fraction of potato proteins are absorbed. Also, LMW-depleted potato juice, such as obtained after selective absorption of the LMW-fraction of potato proteins, can conveniently be used, in which case essentially only the HMW-fraction of potato proteins is present. In that case, this mode entails selective absorption of the HMW-fraction of potato protein from LMW-depleted potato juice.

This mode of the invention comprises in step a) a pH-adjustment step wherein the pH of the potato juice is adjusted to between 4.0 and 6.5, preferably 5.2. Subsequently, in step b) the potato juice is contacted with a functionalised support carrier in which at least 90% of pores have a pore diameter between 10 and 200 nm, and wherein the carrier is functionalised with a hydrophobic, mixed-mode ligand having a pKa 2.5-5, preferably 4-5, which ligand is coupled to the carrier through an S- or O atom, preferably a thioether group. In this embodiment, step b) results in the absorption of both the HMW and the LMW fraction of potato proteins, if present. In step c) the potato proteins present in potato juice can be eluted as a single protein fraction comprising both the HMW- and the LMW-fraction by acidic elution or alkaline elution at pH<3 or pH>9. Also in this case, acidic elution results in protein products with superior quality with respect to colour, odour and taste.

Alternatively for this mode of the invention, in step c) selective elution can be performed. In this case, in step c), desorbing a potato protein fraction from the functionalised support carrier is performed by first selective elution of the HMW-fraction of potato protein at pH 5.7-6.3, preferably 6.0. Subsequently, selective elution of an LMW-fraction of potato protein, if present, can occur at pH lower than 3 by acidic elution, or at pH higher than 9 by alkaline elution as described above. When LMW-depleted potato juice is used in this embodiment, a higher elution pH can be used, such as pH 5.7-8.9, preferably 8.0, which increases elution efficiency of the HMW-fraction.

Generally, in step a) of the present invention, the pH of the potato juice is adjusted to 4.0-6.5, preferably 5.2 for absorption to the functionalised support carrier of all potato protein fractions present in the potato juice, and subsequent elution of a potato protein fraction. Alternatively, the pH of the potato juice is adjusted to 4.0-6.5, preferably 6.0 for selective absorption of the LMW-fraction of potato protein.

Adjusting the pH of potato juice to 4.0-6.5 can be done using various acids and/or bases known in the art, in concentrated or diluted form or combined to result in a buffer. Consequently, various types of strong acids can be used, such as hydrochloric acid, sulphuric acid, nitric acid. Also, weak acids can be used, such as phosphoric acid, formic acid, acetic acid, citric acid, lactic acid. Also, it may be possible that a pre-treatment of potato juice has the result that adjustment to higher pH is required. In that case preferred strong bases are for instance sodium hydroxide, potassium hydroxide, calcium hydroxide. Preferred weak bases are for instance sodium and potassium salts of carbonate, phosphate, acetate, citrate, (bi-)sulphite. When buffers are used, combinations of above-mentioned or other weak acids and weak bases as known in the art are used to adjust the potato juice to the required pH.

In general, preferably strong acid and/or base is used for adjusting the pH, most preferably hydrochloric acid and/or sodium hydroxide. Another, much preferred acid for adjusting the pH is formic acid, especially when a lower chloride content is sought.

In step b) of the present invention, the potato juice is contacted with a functionalised support carrier. The support carrier can have multiple forms or shapes, as long as it allows for sufficient contact with the potato juice to allow absorption. The support carrier may take any shape, such as a spherical, bean, drop or ellipsoid shape, and include among others a bead, particle or grid, but other shapes are conceivable by those skilled in the art. Preferably, the support carrier is essentially spherical, and is in the form of particles. Preferred particles or beads have a bead size of 50-150 μm radius. This bead size provides a good balance between absorption capacity, which is higher for lower bead size, and sensitivity for process parameters such as pressure, and cost.

An important aspect of the support carrier is that it is a porous material. Pores, however, may be filled or coated with a hydrogel. In particular, the support carrier should contain pores, at least 90%, preferably 95% and more preferably 98% and most preferred at least 99% of which have a lower pore diameter limit of 10 nm and an upper pore diameter limit of 200 nm. Thus, a pore diameter between 10 and 200 nm is understood to mean that at least 90%, preferably 95% and more preferably 98%, and most preferred at least 99% of all pores have a pore diameter between 10 and 200 nm. Preferably, the pores have a lower pore diameter limit of 20 nm and an upper pore diameter limit of 150 nm, preferably 100 nm, and even more preferably the pores have a lower pore diameter limit of 30 nm and an upper pore diameter limit of 100 nm, preferably 75 nm. The pore diameter is conveniently determined by porosimetry using mercury intrusion, which is a well-known technique to the skilled person.

Also, a porous material in this respect is a material in which the porosity, defined as the total pore volume of all pores with a diameter smaller than 150 nm is between 0.5 ml/g and 1.5 ml/g. Preferably the porosity is 0.7-1.1 ml/g. Porosity, with respect to this invention, is also determined by mercury intrusion.

For the scope of the present invention, the pore diameter and porosity of the support carrier is of high importance. However, the support carrier may be mounted on a suitable core, so that the support carrier covers most or all of the core. Alternatively, the support carrier may be described by a core material essentially covered by a coating of the porous material. Such cores may be used for various reasons, such as for decreasing the amount of porous material required or changing the density or weight of the particle. The core may be of any material to achieve these targets, including polymeric or metallic materials, as well as inorganic materials such as metal oxides. Preferably, tungsten carbide (WC), iron or magnetite, are used as a core material. The ratio of core to support carrier may be anything, as long as the full particle fulfils the criteria of sufficient porosity and retains the possibility to be functionalised with a suitable ligand as described below. A functionalised support carrier according to the invention is obtained by reacting suitable ligands with the support carrier, thereby obtaining a functionalised support carrier for use in the present invention.

A prerequisite for sufficient contact to allow adsorption is using a support carrier with a pore diameter of 10-200 nm, preferably 10-150 nm, more preferably 20-100 nm, and even more preferably 30 to 75 nm. A smaller pore diameter is found to hamper absorption, whereas larger pores result in lower contact surfaces with low adsorption capacity of especially the HMW fraction as a result. The material of which the support carrier is made is less important, provided the mentioned characteristics are fulfilled. Thus, the material may be any polymer or biomaterial that is stable under the process conditions and can be prepared to have pores with a pore diameter as described while being functionalised with at least one hydrophobic, mixed-mode ligand having a pKa 2.5-5, which is coupled to the carrier through a an S- or O atom, preferably a thioether group.

A support carrier for the ligand can be a porous synthetic polymer, a porous polysaccharide, a porous inorganic material, or any combination thereof. Preferably, a support carrier may be made from porous synthetic polymers such as polymethyl methacrylate (PMMA), polyacryl amide, polymethacrylate or polystyrene, porous polysaccharides like cellulose, dextran or agarose and/or porous silica, controlled pore glass or hydroxyapatite. Most preferably however, agarose and/or PMMA are used as the support carrier.

A support carrier comprising a combination of a porous solid material, such as porous inorganic material, such as ceramic, with a porous hydrogel material, among which for instance certain porous polysaccharides such as agarose may also be used.

The ligands to be attached to the support carrier are of high importance to achieve sufficient adsorption of potato proteins to the functionalised support carrier. Suitable ligands are hydrophobic, mixed mode ligands. This means that their behaviour is based on a combination of electrostatic and hydrophobic interactions. Hydrophobicity of the ligand is important for binding the HMW-fraction of potato protein. Hydrophobic ligands are known in the art, they can be any non-water miscible group, i.e., non-polar. It was found that hydrophobic groups as described below allow for putting the invention in practice.

It was found that patatin prefers a slightly hydrophobic environment, and therefore adsorbs to a functionalised support carrier with a certain degree of hydrophobicity. Hydrophobic ligands are known in the art, and may comprise aromatic or heteroaromatic groups, as well as other hydrophobic molecular components. However, when using only hydrophobic ligands without other functionality, absorption of the HMW fraction, as well as absorption of contaminating coloured species among which phenols is observed. This has a negative impact on the isolation of the HMW fraction of potato protein. For this reason, other functionality to prevent contamination is also desired.

It was also found that the pKa of the ligand on the support carrier of between 2.5 and 5, preferably between 4 and 5, is beneficial to proper absorption of potato protein to the functionalised support carrier. Thus preferably, a carboxylic acid group is present in a ligand for use in a functionalised support carrier according to the present invention, but alternatively, other ligands and spacers with a pKa in this range may be used.

When a hydrophobic ligand with a pKa between 2.5 and 5.0 is used, the LMW fraction of potato proteins is capable of adsorbing to the functionalised support carrier. This pKa-range has the advantage that elution of a potato protein fraction can occur using a weakly acidic solution or buffer. Elution at high pH induces coloration of the isolated potato protein fraction, which is preferably avoided. Also, elution at lower pH than 2.5 may require the presence of a strong acid and/or a high amount of salt, which creates expensive waste streams and may affect the quality of the isolated potato protein isolate. It is preferred that the pKa of the ligand is between 2.5 and 5, because under these conditions the balance between the drawbacks of elution at low and at high pH as mentioned is optimal, resulting in optimal performance.

It was further found that the use of a functionalised support carrier having a pKa between 2.5 and 5, such as a carrier bearing acid groups, greatly reduces absorption of contaminating species to the functionalised support carrier.

With the combination of the proper pKa range and the proper hydrophobicity, it was found that both the HMW and the LMW fraction can absorb to the functionalised support carrier, without significant absorption of contaminating species such as (polymeric) phenols and other coloured species. This is a distinct improvement in comparison to positively charged (mixed mode-)anion exchange and hydrophobic interaction resins.

In particular, the pKa of the ligands should preferably be between 2.5-5, more preferably 4-5. Ligands may be aliphatic, substituted aliphatic or aromatic ligands, including substituted and/or heteroaromatic groups, or combinations thereof. Suitable aromatic groups are for instance substituted or unsubstituted phenyl, naphtyl, pyridine and pyrimidine structures.

For this reason, a ligand that can be used to functionalise the support carrier is a hydrophobic, mixed-mode ligand having a pKa 2.5-5. This ligand should be coupled to the carrier through a S- or O-atom, preferably through a thioether group.

Preferably, these ligands are selected from the group of substituted pyridines, benzoic acids, salicylic acids, nicotinic acids or naphthoic acids, whereby one substitution is at an available ring position with a $(CH_2)_n$—XH group, with n=0-4 and X=O or S. Preferably, these ligands are selected from the group of $(CH_2)_n$—SH substituted pyridines, benzoic, salicylic and nicotinic acids, with n=0-4. Even more preferably these ligands are selected from the group of mercapto-substituted benzoic, salicylic and nicotinic acids (mercapto groups being equal to thiol groups). Most preferred ligands however are 4-mercaptobenzoic acid and 2-mercaptonicotinic acid (2-mercaptopyridine-3-carboxylic acid), with 4-mercaptobenzoic acid being currently considered best among these two most preferred ligands.

The ligands should be coupled to the support carrier through an S- or O atom, for instance by a thioester, thioether, ether or ester group. This means the ligand is coupled to the carrier through a coupling group containing an S or O atom in the backbone.

Preferably a sulphur-containing coupling group is used, such as a thioether or a thioester coupling group. Preferably, a thioether group couples the ligand to the support carrier (by a sulphide bridge, —S—). This is important because it was discovered that both coupling through an S or O-atom, but especially through an S-atom by use of a thioether group, results in resistance to degradation by potato juice of any type. In contrast, the presence of a nitrogen heteroatom in a coupling group, such as for instance an amine or amide group ("N-coupled"), results in faster degradation of the functionalised support carrier in the presence of potato juice. In case multiple heteroatoms are present in a group connecting the ligand with the carrier, it is preferred if at least half of the heteroatoms are S and/or O atoms, more preferably at least ¾th, and most preferably nitrogen atoms are not present in the backbone. Heteroatoms include S, O, P and N atoms.

Ligands coupled through an oxygen-containing group, such as esters or ethers, and preferably ethers, display increased resistance against degradation (or oxidation, modification, discoloration, etc.), but do degrade, albeit slower than amine or amide coupled ligands.

However, oxygen-coupled ligands, especially ethers, are not as stable as sulphur-coupled ligands, preferably thioethers. Sulphur-coupled ligands, in particular those in which the ligand is coupled to the support carrier through a thioether group, display particularly high resistance against degradation by potato juice, and are therefore especially favoured for use in the isolation of potato proteins from potato juice by absorptive processes.

At the same time, oxygen-coupled ligands have lower HMW-binding capacity than sulphur-coupled ligands, in particular thioethers. This may be explained by sulphur having approximately equal electronegativity to carbon, so that the connecting bonds between the support carrier and the ligand have only minor polarisation, which is important for maximising hydrophobicity of the ligand.

For these reasons, sulphur-coupling or oxygen coupling of the ligand to the support carrier is preferred and nitrogen-coupling of the ligand to the support carrier is not preferred. Between sulphur coupling and oxygen coupling, sulphur coupling is preferred. Most preferably, a thioether coupling of the ligand to the support carrier is preferred over oxygen coupling.

Optionally, the ligand can be attached to the support carrier through the use of a spacer. Spacers should be suitable to engage in covalent binding to the polymeric support carrier through an O or an S atom, and to the ligand through an O or an S atom. Spacers used for coupling the ligand to the polymeric support carrier preferably do not comprise many nitrogen atoms in the backbone. In case further heteroatoms are present in the backbone of the spacer, at least half of the heteroatoms are S or O atoms, preferably at least ¾th. Most preferably, spacers used for coupling the ligand to the polymeric support carrier do not comprise nitrogen atoms in the backbone.

Spacer groups are preferably sufficiently stable towards acidic and basic environments and resistant towards reducing conditions in potato juice obtained by the addition of sulphite. Such spacers are highly stable toward the components comprised in potato juice, or the process stream in general. Spacers that can be used to couple the ligands of the present invention include those comprising epoxides and thiiranes, haloacetyl and alkyl halide derivatives, acryloyl derivatives and/or arylating agents. Preferably, spacers that do not induce much extra polarity are used for the coupling, such as epoxides and thiiranes. The skilled person is capable of thinking of more spacers that will result in O- or S-couplings between ligand and polymeric support carrier, with at least one of those couplings being affected through a thioether group, and such spacers are not to be excluded from the present invention.

The ligand should be attached to the support carrier in sufficient amounts to achieve high protein binding capacity. This means that in general, suitable ligands are attached to the support carrier in amounts of 10-200 meq/l, preferably 10-120 meq/l, and more preferably 30-80 meq/l. This can be determined by well-known methods for determination of the exchange capacity, an example of which is described below.

In a further aspect of the present invention, the binding capacity of the functionalised support carrier to absorb potato proteins should be high enough to allow for industrial-scale isolation of potato proteins. For this reason, the absorption capacity of the functionalised support carrier should be at least 25 g/l total protein from PFJ, preferably at least 30 g/l. Also, a functionalised support carrier should be capable of absorbing at least 20 g/l HMW-potato proteins from LMW-depleted PFJ, preferably at least 25 g/l. The binding capacity of the functionalised support carrier is determined by determination of the exchange capacity.

In step c) of the present invention a protein fraction is desorbed from the functionalised support carrier by elution. This is preferably done by the use of an aqueous buffer of fixed pH, which can elute a protein fraction, optionally selectively, based on its isoelectric point (IEP). Buffers for use in the present invention can comprise any weakly acidic or weakly basic compound, as well as combinations with strong acids. Acidic elution of LMW potato protein is preferred over alkaline elution to avoid browning and de-amidation of the protein. Furthermore, elution of LMW potato protein by high salt content buffer is not preferred due to waste water or buffer recycling issues. Preferably, buffers for elution of an HMW-fraction include citrate, acetate, carbonate or phosphate buffers. Buffers for elution of an LMW fraction may include formic, acetic, lactic, maleic, malonic, malic, citric and/or phosphoric acid, or combinations of weakly acidic buffers with strong acids like hydrochloric or sulphuric acid. Preferably however, both an LMW- and an HMW-fraction, as well as a combination thereof, is eluted with a phosphoric acid buffer, or a mixture of formic acid and hydrochloric acid.

Where the pH of the potato juice needs adjustment during processing, such as for instance to lower pH, or to higher pH, acid or base is used to adjust the pH. Such acids and bases for pH-adjustment of potato juice may advantageously be weak acids, such as for instance citric, lactic, formic, acetic or phosphoric acid, or strong acids like nitric acid, hydrochloric and/or sulphuric acid. Also, it may be possible that during processing of potato juice adjustment to higher pH is required. In that case preferred strong bases are for instance sodium hydroxide, potassium hydroxide or calcium hydroxide. Preferred weak bases are for instance sodium and potassium salts of carbonate, phosphate, acetate, citrate and (bi-)sulphite. When buffers are used, combinations of above-mentioned or other weak acids and weak bases as known in the art are used to adjust the potato juice to the required pH.

In step d) of the invention an eluted protein fraction as described above may be further purified downstream by for instance (ultra)filtration, centrifugation, sedimentation, microfiltration, precipitation and various forms of chromatography, such as for instance ion exchange chromatography, gel filtration, affinity chromatograph, hydrophobic interaction chromatography and reversed phase chromatography. Furthermore, absorption chromatography may be applied using different ligands to further purify the protein fraction obtained.

Preferably, the native potato protein fraction is concentrated by ultrafiltration. The choice of the ultrafiltration membrane material can strongly influence the selectivity. Preferably, the ultrafiltration membrane comprises regenerated cellulose, polyethersulphones (PES) and polysulphones (PS). Protease inhibitors isolates may be concentrated using PES or PS-based membranes with a molecular cut-off of 2-20 kDa, and to some extent 30 kDa. Patatin isolates may be concentrated using PES or PS based membranes with a molecular cut-off of 5-30 kDa or a regenerated cellulose based membrane with a molecular cut-off of 5-30 kDa. These membranes can be implemented as tubular, spiral wound, hollow fibre, plate and frame, or as cross-rotational induced shear filter units.

Patatin isolates are ultrafiltrated at pH values of 4.0-8.0, preferably pH 6.0-7.5. For protease inhibitor isolates pH values of 3-7, preferably 3.2-4.5 are used. After removal of impurities the pH may be increased to pH 7-10 to enable high fluxes through the membranes. Protease inhibitors are preferably processed at low pH of 3.0-5.0.

Apart from the purification steps, the native potato protein isolates obtained by the process of the invention may be concentrated up to more than 20% dry matter by evaporation, freeze concentration, or isoelectric precipitation using carbon dioxide. The dry matter of these concentrates can contain more than 85% of protein, preferably more than 90% of protein, based on the nitrogen level (Kjeldahl nitrogen content times 6.25). The dried products can contain more than 90%, preferably more than 92% of protein, with a moisture level of 4-9%.

In a further aspect, the invention is directed at the native potato protein fraction obtainable by the process according to the invention. This native potato protein fraction can be the total native potato protein fraction, the native potato protein patatin fraction, or the native potato protein protease inhibitor fraction, or any combination or subfraction thereof. These potato protein fractions are characterised by their high degree of purity and stability. The total native potato protein fraction of the invention can have an isoelectric point above 4.5, a molecular weight of more than 4 kDa. The potato protein fraction is preferably essentially free of potato-derived organic acids and amino acids.

The native potato protein patatin fraction of the invention can have an isoelectric point of below 5.8, preferably 4.8-5.5, a molecular weight of more than 30 kDa, preferably more than 35 kDa.

The native potato protein protease inhibitor fraction of the invention can have an isoelectric point above 5.5, preferably above 5.8, a molecular weight of below 35 kDa, preferably 4-30 kDa.

Dry native potato proteins can be obtained by spray drying, flash drying or freeze drying. A patatin fraction, a protease inhibitor fraction and a total potato protein fraction are set at a suitable pH to ensure good water solubility. The pH of the concentrates is set to 7.0-9.0, preferably to 7.0-8.0. Concentrates of protease inhibitors can be spray dried using both low pH (3.0-4.0) as well as high pH values (7.0-9.0). The native potato proteins thus obtained have a water solubility of more than 90%, preferably more than 95% at a pH of 7.0 and a temperature of 25° C. Solubility is expressed as the percentage of protein in the supernatant after centrifugation of the solution.

In a preferred embodiment, the native potato protein isolate as obtained after ultrafiltration concentration has a protein content of more than 75% of the dry matter content. The protein content herein is defined as Kjeldahl nitrogen content times 6.25. Preferably the protein content in the native potato protein isolate is more than 80%, more preferably more than 90%, and even more preferably more than 95%.

The native potato protein isolates of the invention may be characterised by a two-dimensional gel electrophoresis analysis combined with an identification of the key proteins in the isolate using MALDI-TOF mass spectrometry analysis. The proteins can be separated in the two-dimensional gel electrophoresis using a pH gradient from 3 to 8 and a molecular weight of 5-100 kDa.

For using the invention, the functionalised support carrier is immobilised by for instance mounting it in a column, hose or pipe while the potato juice is flowed past or through. In such an embodiment, absorption is most likely achieved by a continuous or semi-continuous process, such as for instance packed bed chromatography, expanded bed chromatography, membrane adsorbers or magnetically stabilized bed chromatography. Also, the functionalised support carrier may be mounted in such pipe in the form of a grid through which the potato juice streams to be contacted with the functionalised support carrier. Other means are readily conceivable by those skilled in the art, and are not to be excluded.

In another aspect of the invention, the functionalised support carrier is contacted with the potato juice by combining the potato juice and the support carrier in a single vessel, in which case such mixture may be stirred, shaken or otherwise physically mixed to increase the contact between support carrier and potato juice. In such an embodiment, absorption of potato proteins is most likely a batch process, which is advantageous when highly viscous protein solutions are used.

However, any means of contacting the potato juice with the functionalised support carrier will do, provided contact is intense enough to allow absorption of potato proteins to the functionalised support carrier that has porosity as described and allows attachment of at least one hydrophobic, mixed-mode ligand having a pKa 2.5-5, which is coupled to the carrier through an S- or O atom, preferably a thioether group.

The invention will now be illustrated by the following, non-restrictive Examples.
Methods
Functionalisation of the Support Carrier
Principle The functionalisation of epoxy activated Sepabead EP (or HFA) support carrier which were obtained from Resindion, Binasco, Italy, with ligand takes place at a pH equal or greater than 8.5 depending on the coupling group. Ligand solutions used for functionalisation of the support carrier are set to a fixed pH as follows: the pH of a solution of mercapto-functionalised ligand is set to 8.5, the pH of a solution of amino-functionalised ligand is set to 9.5 and the pH of a solution of hydroxy-functionalised ligand is set to equal or greater than 11. If the ligand does not dissolve at the desired pH, the pH is increased until the ligand dissolves completely.
Method Ligand (1 M, Sigma Aldrich, Zwijndrecht, Netherlands) is dissolved in 250 mL demi water by adding potassium hydroxide 5 M until the desired pH is reached. The solution of mercapto- or amino-substituted ligands is buffered with 100 mM borate. The coupling reaction of hydroxy-functionalised ligands is carried out at pH 11 without the addition of a buffer. During the dissolution of the ligand the pH is adjusted and demi water is added until the ligand is completely dissolved at the desired pH and volume of 300 mL. The ligand solution is allowed to attain room temperature before adding the support carrier.

Epoxy activated Sepabead EP support carrier (100 mL, Resindion, Binasco, Italy) is washed with demi water in a glass filter until the conductivity is lower than 10 µS/cm and excess of water is removed by running it under vacuum conditions. Then, the support carrier is transferred to a 500 mL flask with the ligand solution, closed with a ground stopper and incubated overnight at 175 rpm. The pH is checked after 1 hour and the next morning.

After rinsing the excess of ligand with 100 mM sodium hydroxide the remaining epoxy groups are hydrolyzed by incubating the functionalised support carrier in 1 M of sodium hydroxide at 50° C. for 2 hour. The functionalised support carrier is stored in 50 mM sodium hydroxide at 4° C. The PMMA- and agarose support carriers used in Example 2 are epoxy-activated, and thus could be functionalised with 4MBA according to the same principle and method as described for Sepabead EP and HFA above.

Sartobind epoxy activated membrane units were functionalized according to the manufacturers instructions (Sartorius Stedim Biotech, Goettingen, Germany).

Calculation of the pKa

The pKa of the labeled ligand is calculated with MarvinSketch (2011) 5.4.1.1 software from ChemAxon with the pKa options listened in Table 1. The possible alteration of the electron distribution caused by the labelling which could influence the pKa of the anionic group is taken into account by calculating the pKa with the epoxy group of the functionalised support carrier.

TABLE 1

The selected $pK_a$ options to calculate the $pK_a$ in MarvinSketch

| Mode | macro |
| Acid/base prefix | static |
| Min basic $pK_a$ | −10 |
| Max acidic $pK_a$ | 20 |
| Temperature (K) | 298 |
| Consider tautomerization | no |

Total Exchange Capacity

The principle of the total exchange capacity is to neutralize protonated anionic groups with an excess of base (neutralization liquid). The exchange capacity of the functionalised support carrier is determined with back titration of the base with hydrochloric acid as titrant.

Conditioning of the Functionalised Support Carrier (Protonation of the Anionic Group)

The functionalised support carrier is packed into a column with a diameter of 1 cm and a bed height of 16 cm; this dimension corresponds to a bed volume of 12 mL. If it is required to clean the functionalised support carrier thoroughly the functionalised support carrier is cleaned with 50 mL sodium hydroxide 1 M followed with 150 mL sodium hydroxide 100 mM at 10 mL/min. The functionalised support carrier is rinsed with 200 ml water at 10 mL/min.

The ligand on the functionalised support carrier is protonated with 200 mL hydrochloric acid 100 mM at 10 mL/min. The excess of acid is rinsed with 200 mL water at 10 mL/min or until the conductivity is <10 μS/cm.

Neutralization of the Anionic Group

The void volume is removed by pulling a 50 mL syringe vacuum and transfer quantitative the functionalised support carrier with 200 mL neutralization solution of 30 mM sodium hydroxide into a 300 mL flask. A ground stopper is put on the flask and it is shaken for at least 1 h at 175 rpm.

Titration

The sodium hydroxide consumption of the ligand/functionalised support carrier can be determined by the concentration of the neutralization solution of 30 mM sodium hydroxide and the concentration after the neutralization (back titration). Therefore 25 mL of the neutralization solution and 25 mL of the partial neutralized neutralization solution is titrated with titrant 100 mM HCl. The equivalence point of the classic acid-base titration is the point of inflection of the S-shaped titration curve.

Correction for the Systematical Error and the Formation of Carboxyl Group by the Oxidation of Methacrylate The volume left behind after pulling the Sepabead functionalised support carrier dry with a 50 mL syringe is estimated on 68% which is 7 mL of the suggested volume of 12 mL (3.5 mL removed by syringe). The remaining volume dilutes the neutralization liquid from 30 mM to 29 mM, which is equal to a systematical error of 15 meq/L. To correct for the systematical error and the formation of carboxyl groups by the oxidation of the methacrylate support carrier during labeling a hydrolyzed Sepabead functionalised support carrier (blanco) is titrated on the same way as the labeled Sepabead support carrier.

Calculation $$TEC = \frac{(V_{titr,sample} - V_{titr,neutralisation}) \cdot c_{HCl} \cdot V_{flask} \cdot 1000}{V_{resin} \cdot V_{sample}}$$

$$TEC_{corr,sample} = TEC_{sample} - TEC_{unlabled\ support\ carrier}$$

where:

TEC=total exchange capacity (meq/L)

$TEC_{sample}$=total exchange capacity sample without systematical error correction. (meq/L)

$TEC_{corr.\ sample}$=total exchange capacity corrected for systematical error (meq/L)

$TEC_{unlabeled\ support\ carrier}$=total exchange capacity blank/systematical error (meq/L)

$V_{titr\ sample}$=titration volume sample (or blank) (mL)

$V_{titr.\ neutralization}$=titration volume neutralization solution (mL)

$C_{HCl}$=concentration HCl (mmol/mL)

$V_{flask}$=Volume NaOH added to flask (250 mL)

$V_{sample}$=Volume sample (25 mL≈25.0 g)

Pore Size and Pore Volume Determination

The pore size and pore volume of the used Sepabead support carriers has been determined by use of the mercury intrusion porosimetry on a Micromeretics ASAP2400 porosimetry system according to a standardised procedure well-known in the art.

Protein Adsorption Experiments

The adsorption experiments are carried out according to the following procedure to keep the experiments as uniform as possible. LMW stands for the low molecular weight fraction of potato proteins predominantly consisting of protease inhibitors, whereas HMW stands for the high molecular weight fraction of potato proteins predominantly consisting of patatin.

A representative batch of potato fruit juice (PFJ) and of LMW-depleted PFJ (Avebe, Gasselternijveen, The Netherlands) was frozen so that accurate comparison of the capacity and the affinity of each ligand for the selective elution and selective adsorption processes could be determined without introducing uncertainty based on the natural variation in the concentration of proteins. Before an experiment, the frozen PFJ (or LMW-depleted PFJ) is thawed at 4° C. followed by further thawing in a water bath at 28° C. as required. The PFJ (or LMW-depleted PFJ) is set to the desired pH and centrifuged for 5 minutes at 4600 g to remove remnant solids.

The functionalised support carrier is packed in a column with an internal surface of 1.767 $cm^2$ and with a bed height of 34 cm corresponding to a bed volume of 60 $cm^3$. The flow is set to 10 cm/min. The support carrier is equilibrated with equilibration/wash buffer sodium citrate 30 mM with the desired adsorption pH of 5.2 or 6.0 until the column reaches the desired pH. For total protein adsorption 6 Bed Volumes (BV) of PFJ pH 5.2 is loaded. For selective adsorption of LMW potato proteins from PFJ (pH 6.0) or HMW potato proteins from LMW depleted PFJ (pH 5.2) 9 BV were loaded.

The column is washed with the equilibration/wash buffer of 30 mM Sodium citrate for approximately 2.5 BV to remove the non-adsorbed components. The adsorbed protein may be eluted with a desired eluens followed by a complete desorption of all remaining proteins with sodium hydroxide.

Total protein binding at pH 5.2:
  Equilibrate the column with 30 mM sodium citrate (pH 5.2) until pH 5.2 is achieved.
  Load 6 BV PFJ and collect the feed.
  Wash with approximately 2.5 BV equilibration buffer 30 mM sodium citrate pH 5.2 to remove the non-adsorbed components and collect the wash to construct a mass balance.
Protein Isolation by Alkaline Elution:
  Sodium hydroxide elution:
    Elute with 50 mM sodium hydroxide and start eluent collection when OD280 slope>60 mAU/min.
    Hold until pH>9.5, OD280<150 mAU, slope OD280>−50 mAU/min and stop collecting. Continue for 0.25 BV.
  Clean the column with 1.5 BV sodium hydroxide 1 M.
  Replace the 1 M sodium hydroxide solution in the column with 0.5 BV of 50 mM sodium hydroxide for storage purpose.
HMW Isolation at pH 5.2 Through Selective Absorption:
  Equilibrate with 30 mM sodium citrate buffer (pH 5.2) until pH 5.2 is achieved.
  Load 9 BV LMW-depleted PFJ and collect the feed.
  Wash with approximately 2.5 BV equilibration buffer 30 mM sodium citrate pH 5.2 to remove the non-adsorbed components and collect the wash to construct a mass balance.
  Sodium carbonate elution:
    Elute with 100 mM sodium carbonate pH 8.0 and wait for collection until OD280 slope>60 mAU/min.
    Hold until pH>6.0, OD280<150 mAU, slope OD280>−50 mAU/min and stop collecting. Continue flow for 0.25 BV.
  Clean the column with 1.5 BV sodium hydroxide 1 M.
  The sodium hydroxide 1 M is replaced with 0.5 BV of 50 mM sodium hydroxide during storage purpose.
LMW Isolation at pH 6.0 Through Selective Absorption:
  Equilibrate with 30 mM sodium citrate (pH 6.0) until pH 6.0 is achieved.
  Load 9 BV PFJ and collect the feed.
  Wash with approximately 2.5 BV equilibration buffer 30 mM sodium citrate pH 6.0 to remove the non-adsorbed components and collect the wash to construct a mass balance.
  Phosphoric acid elution:
    Elute with 50 mM phosphoric acid and wait for collection until OD280 slope>60 mAU.
    Hold until pH<3.5, OD280<150 mAU, slope OD280>−50 mAU/min and stop collecting. Continue flow for 0.25 BV.
  Sodium hydroxide elution:
    Elute with 50 mM sodium hydroxide and wait for collection until OD280 slope>60.
    Hold until pH>9.5, OD280<150, slope OD280>−50 mAU/min and stop collecting and continue for 0.25 BV.
  Clean the column with 1.5 BV sodium hydroxide 1 M.
  Sodium hydroxide 1 M is replaced with 0.5 BV of 50 mM sodium hydroxide for storage purpose.

The protein content is determined with Sprint rapid protein analyzer (CEM company) which was calibrated with the Kjeldahl method with the conversion factor of 6.25 generally used for vegetable proteins. The elution capacity of the functionalised support carrier is expressed in grams protein per liter. The experiments were verified through a protein mass balance by verification of protein concentrations in all streams, among which feed, collect and wash-streams. Recoveries were between 95 and 102% (not shown).

The total protein adsorption is evaluated by the protein adsorption from PFJ at pH 5.2 within 6 bed volumes followed by an alkaline elution of both LMW and HMW protein fractions.

Selective adsorption of HMW is evaluated by protein adsorption from LMW depleted PFJ at pH 5.2 within 9 bed volumes followed by a mild elution using carbonate 100 mM pH 8.0 to prevent alteration of the native proteins.

The percentage HMW proteins present in the obtained eluate (total protein and selectively adsorbed HMW) is determined by analyzing the ratio of >35 kD proteins according to Experion Pro260 Analysis Kit (Bio-rad Laboratories).

The influence of the pKa on the acidic elution is evaluated with a range of ligands with different pKa's. The LMW is adsorbed from 9 BV of PFJ at pH 6.0 and obtained by elution with 50 mM phosphoric acid, followed by a complete elution of the non-desorbed protein with 50 mM sodium hydroxide.

The Stability of the Functionalised Support Carrier in Unstabilized PFJ (Accelerated Fouling)

Unstabilized PFJ
  Fresh tubers are juiced/rasped in a juice centrifuge of Braun. Insoluble fibers are removed by filtering the juice over a buchner funnel with a 595 paper filter. The pH of the PFJ should be pH 6.0±0.5, if not adjust the pH to 6.

Conditioning of the Functionalised Support Carrier
  Normally the functionalised support carrier is stored in 50 mM NaOH therefore it is sufficient to rinse the functionalised support carrier with deionized water until the conductivity is lower than 50 µS/cm. (An equilibration is not necessary, because the endogenous buffer capacity of PFJ will prevent an increase of pH.)
  Fill a Kontes® column (1.0×20 cm) to the top with functionalised support carrier (20 cm≈16 mL)
  Rinse with minimal 100 mL deionized water and continue until the conductivity is lower than 50 µS/cm.
  Dry the functionalised support carrier with a 50 mL syringe.

Cleaning, Storage or Conditioning of the Functionalised Support Carrier for the Second Time.
  Remove the PFJ from the functionalised support carrier by discarding the PFJ over a glass filter pore 3 and rinse the functionalised support carrier with deionized water.
  Place a funnel into the Kontes® column and transfer the functionalised support carrier from the glass filter to the column.
  Elute the protein and color with 250 mL NaOH 50 mM at 10 mL/min.
  The functionalised support carrier can be stored in 50 mM NaOH at 4° C. or rinsed with 250 mL deionized water for the next incubation with PFJ. If the functionalised support carrier will be used for the next incubation, dry the functionalised support carrier with a 50 mL syringe.

Incubation with Unstabilized PFJ
  Fill a graduated cylinder with PFJ until 150 mL.
  From the 150 mL fill a 50 mL syringe with PFJ juice and press the functionalised support carrier out of the kontes column with the syringe into a flask of 300 mL.
  Measure the pH after 1.5 hours and the next morning.
  After one night incubation clean the functionalised support carrier as described above and repeat the incubation at least two times.

The Color Matrix of the Eluted Protein

The color matrix of the eluted protein is expressed as a color/protein ratio where the color adsorption at 310 nm measured spectrophotometrically is divided by the protein concentration measured by Sprint rapid protein analyzer ($\lambda$310 nm/P (%)). Sprint rapid protein analyzer is a well-known and standardised technique in the field of protein concentration analysis, and the color matrix determination at 310 nm comes from a quick protein determination between 280 and 310 nm where the wavelength 310 nm is used for correction of the colored matrix.

Procedure
  Dilute the elution sample with 100 mM borate pH 10.0 until the extinction is between 0.1 and 0.8 and dilute the blank consisting of water the same way.
  Auto-zero the blank and measure the sample at 310 nm.

Calculation $$\lambda 310 / P(\%) = \frac{E_{310} \cdot f}{P(\%)}$$

where: $\Delta 310/P$ (%)=color/protein ratio (%$^{-1}$)
  $E_{310}$=extinction at wavelength 310 nm
  f=dilution factor in borate 100 mM pH 10.0.
  P (%)=protein concentration measured by Sprint (%)

Example 1: Ligand Selection

Results

Figure 2A:
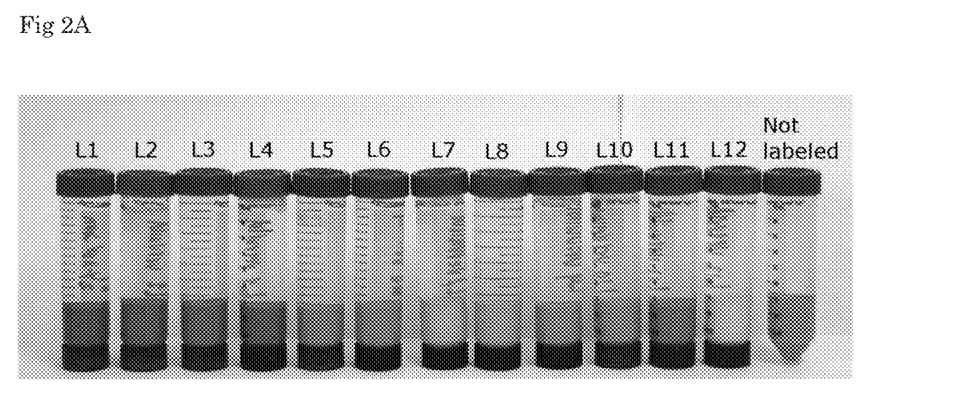
FIG. 2 Coloration of the functionalised support carrier in an accelerated fouling test after 3×24 h incubation with unstabilised potato fruit juice (not containing sulfite) a) with acidic ligands 1-12 and b) with Streamline Direct CST1 and Sepabead HFA with 4MBA-ligands.
Figure 2B:
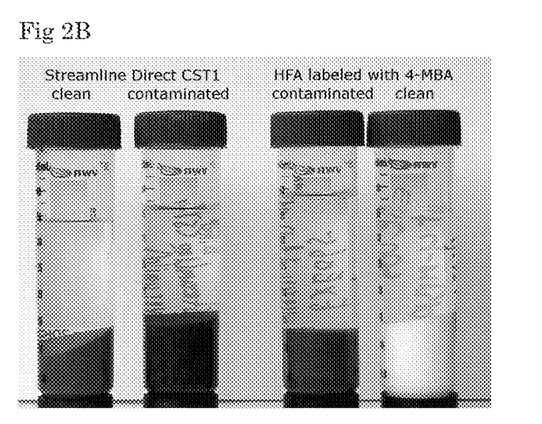

This invention is illustrated by experiments using 11 mixed-mode ligands that have been selected with varying acidity, that are attached on a support carrier with pore size of 30-150 nm. Among these ligands are 10 weak acidic mixed-mode ligands and 1 strong acidic mixed-mode ligand. Furthermore, Streamline Direct CST1 (ligand and spacer composition identical to GE-healthcare Capto MMC) and Sepabeads HFA (exe065) (both containing a nitrogen-containing spacer) functionalised with 4-mercaptobenzoic acid in the same way as described above have been included in these experiments, as has the hydrophobic interaction support carrier Amberlite XAD7HP. These ligands have been tested for the capacity to:
  Adsorb at least 25, preferably >30 g/L total protein from potato juice at pH 5.2 (table 2)
  Adsorb at least 20, preferably >25 g/L HMW potato protein from LMW depleted potato juice at pH 5.2 (table 3)
  Desorb LMW potato protein by acidic elution followed by elution of the non-desorbed proteins by alkaline elution (table 4)
  Resist the (enzymatic-) oxidation in an accelerated aging assay by potato juice without added sulphite. (FIGS. 2 and 3, Tables 5 and 6)

TABLE 2

Total potato protein adsorption capacity (g/L) for support carriers with porosity between 30 and 150 nm functionalised with 11 different acidic mixed-mode ligands, a weak cation exchange resin (a carboxyl acrylic resin) and two hydrophobic resins (phenyl sepharose and XAD7HP). The percentage HMW potato protein in the total protein pool and the (calculated) acidity of each ligand is given in the last two columns.

| No. | Ligand name | Capacity (g/L) | % HMW | pKa |
|---|---|---|---|---|
| 1 | 4-Aminobenzoic acid (4-ABA) | 29.7 | 23.5 | 4.75 |
| 2 | 3-Aminobenzoic acid (3-ABA) | 31.7 | 18.7 | 4.88 |
| 3 | 3-Aminobenzenesulfonic acid (3-ABSA) | 35.0 | 11.7 | −2.68 |
| 4 | 2-hydroxy-4-aminobenzoic acid (4-aminosalicylic acid, 4-ASA) | 33.1 | 17.8 | 3.67 |
| 5 | 3-Hydroxybenzoic acid (3-HBA) | 31.4 | 17.4 | 3.84 |
| 6 | 2,4-Dihydroxybenzoic acid (2,4-DHBA) | 31.6 | 15.0 | 3.08 |
| 7 | 4-Hydroxybenzoic acid (4-HBA) | 27.5 | 17.3 | 4.36 |
| 8 | 2-Mercaptopyridine-3-carboxylic acid (2-Mercaptonicotinic acid (2-MNA) | 38.6 | 22.6 | 3.70 |
| 9 | 4-mercaptobenzoic acid (4-MBA) | 39.1 | 33.1 | 4.10 |
| 10 | 6-hydroxy-2-naphthoic acid (6-H2NA) | 26.2 | 20.9 | 3.99 |
| 11 | 3,5-dihydroxy-2-napthoic acid (3,5-H2NA) | 34.0 | 20.0 | 2.69 |
| 12 | carboxyl (acrylic resin) | 10.8 | 8.5 | 3.90 |
| 13 | phenyl sepharose | 7.8 | 34.6 | N/A |
| 14 | Amberlite XAD7HP | 9.2 | 8.0 | N/A |
| 15 | StreamLine Direct CST1 | 39.9 | 19.0 | 3.61 |

It follows that the capacity of the anionic mixed mode ligands for potato protein absorption is roughly between 30 and 40 g/L, while the carboxyl acrylic resin has 11 g/L and the hydrophobic interaction resins (XAD7HP & phenyl sepharose) have low capacity of 8-9 g/L. Thus, absorption capacity of the anionic ligands is much higher.

TABLE 3

HMW potato protein adsorption capacity (g/L) from LMW-depleted potato juice at pH 5.2 for 11 acidic mixed-mode ligands, one mixed-mode ligand coupled through a nitrogen-containing spacer (CST1), a weak cation exchange resin (carboxyl acrylic resin) and two hydrophobic resins (phenyl sepharose and XAD7HP). The corresponding HMW content (% HMW, expressed as % proteins > 35 kDa) of the obtained HMW potato protein is given in the last column.

| No. | Ligand | Capacity (g/L) | % HMW |
|---|---|---|---|
| 1 | 4-Aminobenzoic acid | 19.8 | 77.9 |
| 2 | 3-Aminobenzoic acid | 22.0 | 84.1 |
| 3 | 3-Aminobenzenesulfonic acid | 14.0 | 85.1 |
| 4 | 2-hydroxy-4-aminobenzoic acid (4-aminosalicylic acid) | 19.5 | 90.8 |
| 5 | 3-Hydroxybenzoic acid | 16.5 | 86.0 |
| 6 | 2,4-Dihydroxybenzoic acid | 15.8 | 82.0 |
| 7 | 4-Hydroxybenzoic acid | 13.9 | 80.1 |
| 8 | 2-Mercaptopyridine-3-carboxylic acid (2-Mercaptonicotinic acid) | 24.6 | 79.6 |
| 9 | 4-mercaptobenzoic acid | 30.5 | 84.8 |
| 10 | 6-hydroxy-2-naphthoic acid | 16.7 | 77.5 |
| 11 | 3,5-dihydroxy-2-napthoic acid | 20.9 | 94.4 |
| 12 | carboxyl (acrylic resin) | 0.9 | 82.0 |
| 13 | phenyl sepharose | 2.5 | 85.3 |
| 14 | Amberlite XAD7HP | 1.9 | 82.4 |
| 15 | Streamline Direct CST1 | 22.8 | 72.1 |

It follows that the highest absorption capacity for the HMW fraction of potato proteins from LMW-depleted potato juice is observed for thioether-coupled ligands.

TABLE 4

LMW potato protein adsorption capacity (g/L) for a strong
(No. 3) and two weak acid mixed-mode ligands (No. 6 & 9).
The percentage LMW protein desorbed by acid elution and subsequent
alkaline elution is shown in the last columns.

| No. | Ligand | Acidity pKa | Capacity (g/L) | % acid | % alkaline |
|---|---|---|---|---|---|
| 3 | 3-Aminobenzenesulfonic acid | −2.68 | 30.0 | 39 | 61 |
| 6 | 2,4-Dihydroxybenzoic acid | 3.08 | 28.0 | 84 | 16 |
| 9 | 4-mercaptobenzoic acid | 4.10 | 40.6 | 83 | 17 |

Acidic elution of LMW potato protein is preferred over alkaline elution to avoid browning and de-amidation of the protein. Furthermore, elution of LMW potato protein by high salt content buffer is not preferred due to waste water or buffer re-use issues. Strongly acidic ligands such as number 3 in this experiment display inefficient elution with weakly acidic buffers. Weakly acidic buffers are preferred to avoid protein denaturation. To allow acidic elution using weakly acidic buffers a weakly acidic ligand, such as numbers 6 and 9 perform best. Hence the use of weakly acidic ligands having pKa between 2.5-5 is preferred.

TABLE 5

Increase of the total exchange capacity after incubation with
potato juice that has not been stabilized with sulphite.

| No. | Ligand | % increase exchange capacity |
|---|---|---|
| 1 | 4-Aminobenzoic acid | 125 |
| 2 | 3-Aminobenzoic acid | 58 |
| 3 | 3-Aminobenzenesulfonic acid | 64 |
| 4 | 2-hydroxy-4-aminobenzoic acid (4-aminosalicylic acid) | 98 |
| 5 | 3-Hydroxybenzoic acid | 30 |
| 6 | 2,4-Dihydroxybenzoic acid | 41 |
| 7 | 4-Hydroxybenzoic acid | 36 |
| 8 | 2-Mercaptopyridine-3-carboxylic acid (2-Mercaptonicotinic acid) | −2 |
| 9 | 4-mercaptobenzoic acid | 11 |
| 10 | 6-hydroxy-2-naphthoic acid | 72 |
| 11 | 3,5-dihydroxy-2-napthoic acid | 65 |
| 12 | carboxyl (acrylic resin) | 2 |
| 13 | phenyl sepharose | N/A |
| 14 | Sepabead HFA with 4MBA | 32 |
| 15 | Amersham Streamline Direct CST I | 106 |

Figure 1:
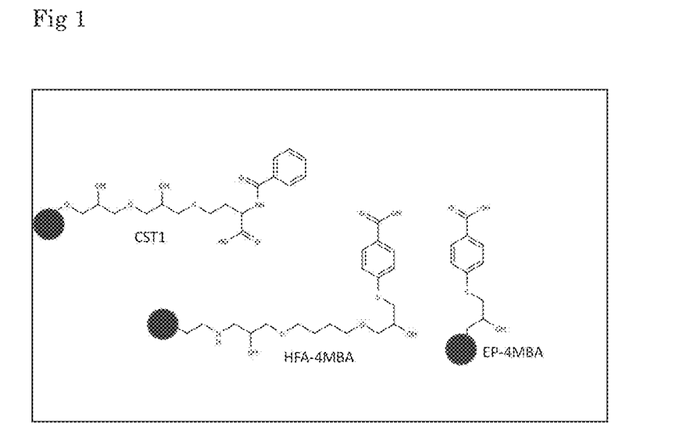
FIG. 1 Structural formulas for the ligands Streamline Direct CST1 (CST1), 4-mercaptobenzoic acid-functionalised Sepabead HFA (HFA MBA), and 4-mercaptobenzoic acid-functionalised Sepabead EP (EP MBA). The support carrier is represented by a filled circle.

Data in table 4 as well as FIG. 1 show that nitrogen-coupled mixed-mode ligands are susceptible to oxidation by potato juice. Potato juice is usually stabilized by the addition of sulphite. However the inhibition of oxidative browning by sulphite is generally not complete and gradual deterioration of the ligand in time can occur. In contrast to amino coupled ligands, oxygen-coupled ligands and especially thioether-coupled ligands are much more stable to degradation by for instance oxidation.

It follows from table 4 that amino-coupled ligands have an average increase in the exchange capacity in accelerated fouling experiments of 86%, hydroxyl-coupled ligands have 49% and thioether-coupled ligands have 5%. Nitrogen-containing spacers also display accelerated fouling (entrees 14 and 15). Thus, nitrogen-containing groups are less suitable for use in the isolation of potato proteins from potato juice. Oxygen-coupled groups have higher resistance to fouling and thioether-coupled groups have the highest resistance to fouling.

TABLE 6

The color/protein (λ310/P(%)) ratio for the same series of
ligand/support carrier combinations. It is determined by dividing color
adsorption at 310 nm by the protein concentration measured by Sprint.

| | | Color/protein ratio (λ310 nm/P(%)) | | | | |
|---|---|---|---|---|---|---|
| | | Total adsorption | HMW adsorption at pH 5.2 | | LMW adsorption at pH 6.0 | |
| no: | Ligand | at pH 5.2 NaOH 50 mM | CO$_3$ pH 8.0 | NaOH 50 mM | H$_3$PO$_4$ 50 mM | NaOH 50 mM |
| 1 | 4-Aminobenzoic acid | 3.1 | 2.3 | 5.1 | | |
| 2 | 3-Aminobenzoic acid | 2.9 | 1.9 | 4.1 | | |
| 3 | 3-Aminobenzenesulfonic acid | 3.0 | 2.7 | 4.7 | 1.1 | 4.9 |
| 4 | 2-hydroxy-4-aminobenzoic acid | 3.2 | 2.1 | 3.8 | | |
| 5 | 3-Hydroxybenzoic acid | 3.4 | 2.6 | 5.4 | | |
| 6 | 2,4-Dihydroxybenzoic acid | 3.3 | 2.6 | 4.3 | 1.3 | 13.6 |
| 7 | 4-Hydroxybenzoic acid | 3.0 | 3.0 | 5.2 | | |
| 8 | 2-Mercaptopyridine-3-carboxylic acid | 2.6 | 1.6 | 3.3 | | |
| 9 | 4-mercaptobenzoic acid | 2.4 | 1.4 | 3.0 | 1.4 | 9.1 |
| 10 | 6-hydroxy-2-naphthoic acid | 3.4 | 2.4 | 3.8 | | |
| 11 | 3,5-dihydroxy-2-napthoic acid | 3.0 | 2.0 | 2.8 | | |
| 12 | Carboxyl acrylic resin | 2.7 | 15.9 | 18.5 | | |
| 13 | phenyl sepharose | 2.3 | 3.2 | 1.7 | | |

It follows that the acidic ligand which has the lowest color/protein ratio is 4-mercaptobenzoic acid both for total protein absorption and for HMW-absorption, and 2-mercaptopyridine-3-carboxylic acid is second lowest. Therefore, thioether-coupled acidic ligands display low affinity for color or phenolic complexes that can cause fouling in the long term and result in a less colored protein eluate.

Example 2: Carrier Selection

TABLE 7

Three functionalised support carrier systems with the same 4-mercaptobenzoic acid ligand but with different porosity have been tested for their capacity to absorb HMW and LMW potato protein. The same procedure as described above was used to determine absorption capacity.

| carrier, ligand | pore diameter | LMW capacity g/L | HMW capacity g/L |
|---|---|---|---|
| 5% agarose, 4-MBA | 50-90 nm | 59 | 32 |
| PMMA-4-MBA | 30-60 nm | 37 | 33 |
| Membrane, 4-MBA | 1-5 μm | 31 | ≤10 |

It follows that the HMW absorption capacity fulfils the criteria at a pore diameter higher than 30 nm, and remains so at least up to a pore diameter of 90 nm. Also, from the difference in material it follows that the pore size is the main parameter for this difference. It is therefore reasonable that pore sizes between 10 and 200 nm, in combination with suitable ligands, will display favorable absorption characteristics. Thus, functionalized support carriers comprising suitable ligands should have pore diameters between 10 and 200 nm, preferably 10-150 nm, more preferably 20-100 nm, and even more preferably 30 to 75 nm.

The invention claimed is:

1. A process for the isolation of a native potato protein fraction from potato juice, comprising the steps of:
   a) adjusting the pH of the potato juice to 4.0-6.5;
   b) contacting the potato juice in a continuous or semi-continuous packed bed reactor with a functionalised support carrier having a porosity, defined as the total pore volume of all pores with a diameter smaller than 150 nm, of between 0.5 ml/g and 1.5 ml/g and wherein the carrier is functionalised with a hydrophobic, mixed-mode ligand having a pKa of 2.5-5;
   c) desorbing the potato protein fraction from the functionalised support carrier by elution; and
   d) optionally concentrating and/or drying the potato protein fraction.

2. The process according to claim 1, wherein the ligand is coupled to the carrier through an S- or O-atom.

3. The process according to claim 1, wherein the functionalised support carrier is immobilized while potato juice flows past or through the immobilized support carrier.

4. The process according to claim 1, wherein the functionalized support carrier is combined with potato juice in a single vessel and physically mixed.

5. The process according to claim 1, wherein the functionalised support carrier comprises pores of which at least 90% have a pore diameter of between 10 and 150 nm.

6. The process according to claim 1, wherein the functionalised support carrier comprises pores of which at least 90% have a pore diameter of between 10 and 150 nm.

7. The process according to claim 1, wherein the functionalised support carrier comprises pores of which at least 90% have a pore diameter of between 20 and 100 nm.

8. The process according to claim 1, wherein elution is carried out at a pH between 5.7 and 8.9.

9. The process according to claim 8, wherein the potato protein fraction is a patatin fraction.

10. The process according to claim 1, wherein elution is carried out at a pH above 9 or below 3.

11. The process according to claim 10, wherein the potato protein fraction is a protease inhibitor fraction.

12. The process according to claim 1, wherein elution is carried out with an aqueous buffer.

13. The process according to claim 1, wherein the mixed-mode ligand is chosen from the group of substituted benzoic acids, salicylic acids, nicotinic acids and naphthoic acids, whereby substitution is at an available ring position with a (CH2)n-XH group, with n=0-4 and X=S.

14. The process according to claim 1, wherein the support carrier is a porous synthetic polymer, a porous polysaccharide, a porous inorganic material, or any combination thereof.

15. The process according to claim 1, wherein the hydrophobic, mixed-mode ligand is attached to the support carrier through a spacer that links to the support carrier through an O or S-atom, which spacer does not comprise nitrogen atoms in the backbone.

16. The process according to claim 13, wherein the pH of the potato juice is adjusted with acid and/or base.

17. The process according to claim 13, wherein the potato juice has undergone a pretreatment comprising absorption of contaminants to a layered silicate and/or activated carbon and/or a flocculation.

* * * * *